(12) United States Patent
Ronaghi

(10) Patent No.: US 6,828,100 B1
(45) Date of Patent: Dec. 7, 2004

(54) METHOD OF DNA SEQUENCING

(75) Inventor: Mostafa Ronaghi, Palo Alto, CA (US)

(73) Assignee: Biotage AB, Uppsala (SE)

( * ) Notice: Subject to any disclaimer, the term of this patent is extended or adjusted under 35 U.S.C. 154(b) by 0 days.

(21) Appl. No.: 09/889,812

(22) PCT Filed: Jan. 20, 2000

(86) PCT No.: PCT/GB00/00146

§ 371 (c)(1),
(2), (4) Date: Dec. 4, 2001

(87) PCT Pub. No.: WO00/43540

PCT Pub. Date: Jul. 27, 2000

(30) Foreign Application Priority Data

Jan. 22, 1999 (GB) .............................................. 9901475

(51) Int. Cl.[7] .............................. C12Q 1/68; C12P 19/34
(52) U.S. Cl. ......................... 435/6; 435/91.1; 435/91.2
(58) Field of Search ........................ 435/6, 91.1, 91.2, 435/810, 91.21, 91.5; 935/17, 77, 78

(56) References Cited

U.S. PATENT DOCUMENTS

| 5,449,603 A | 9/1995 | Nielson et al. |
| 5,547,843 A | 8/1996 | Studier et al. |
| 5,605,824 A | 2/1997 | Nielson et al. |
| 5,646,019 A | 7/1997 | Nielson et al. |
| 5,773,257 A | 6/1998 | Nielson et al. |
| 6,335,162 B1 * | 1/2002 | Shultz ........................... 435/6 |

FOREIGN PATENT DOCUMENTS

| WO | WO93/23564 | 11/1993 |
| WO | WO98/13523 | 4/1998 |
| WO | WO98/2844 | 7/1998 |
| WO | WO98/55653 | 12/1998 |

OTHER PUBLICATIONS

Chou, "Minimizing deletion mutagenesis artifact during taq DNA polymerase PCR by *E.coli* SSB", Nucleic Acids Research, (1992), vol. 20, No. 6, p. 4371.*
Stratagene Catalog, "Gene Characterization kits", (1998), p. 39.*
Nyren et al., "Enzymatic Method for continuous Monitoring of Inorganic pyrophosphate synthesis". Analytical Biochemistry, (1985), vol. 151, pp. 504–509.*
Kaczorowski et al. (1994) *Analytical Biochemistry* 221:127–135.
Nyren et al. (1997) *Analytical Biochemistry* 244:367–373.
Rapley (1994) *Molecular Biotechnology* 2:311–314.
Ronaghi et al. (1996) *Analytical Biochemistry* 242:84–89.
Ronaghi et al. *Science* (1998) 281:363–365.

* cited by examiner

*Primary Examiner*—Kenneth R. Horlick
(74) *Attorney, Agent, or Firm*—Dorsey & Whitney LLP

(57) ABSTRACT

The present invention relates to a method of identifying a base at a target position in a sample nucleic acid sequence wherein a primer, which hybridizes to the sample nucleic acid immediately adjacent to the target position, is provided and the sample nucleic acid and primer are subjected to a polymerase reaction in the presence of a nucleotide whereby the nucleotide will only become incorporated if it is complementary to the base in the target position, and said incorporation is detected, characterized in that, a single-stranded nucleic acid binding protein is included in the polymerase reaction step.

9 Claims, 7 Drawing Sheets

METHOD OF DNA SEQUENCING

The present invention relates to methods of nucleic acid sequencing and in particular to sequencing-by-synthesis methods, ie. those methods based on the detection of nucleotide incorporation during polymerase extension, rather than on analysis of the nucleotide sequence itself, and to the improvements derivable in such methods by the use of a single-stranded DNA binding protein.

DNA sequencing is an essential tool in molecular genetic analysis. The ability to determine DNA nucleotide sequences has become increasingly important as efforts have commenced to determine the sequences of the large genomes of humans and other higher organisms. The two most commonly used methods for DNA sequencing are the enzymatic chain-termination method of Sanger and the chemical cleavage technique of Maxam and Gilbert. Both methods rely on gel electrophoresis to resolve, according to their size, DNA fragments produced from a larger DNA segment. Since the electrophoresis step as well as the subsequent detection of the separated DNA-fragments are cumbersome procedures, a great effort has been made to automate these steps. However, despite the fact that automated electrophoresis units are commercially available, electrophoresis is not well suited for large-scale genome projects or clinical sequencing where relatively cost-effective units with high throughput are needed. Thus, the need for non-electrophoretic methods for sequencing is great and several alternative strategies have been described, such as scanning tunnel electron microscopy (Driscoll et al., 1990, Nature, 346, 294–296), sequencing by hybridization (Bains et al., 1988, J. Theo. Biol. 135, 308–307) and single molecule detection (Jeff et al., 1989, Biomol. Struct. Dynamics, 7, 301–306), to overcome the disadvantages of electrophoresis.

Techniques enabling the rapid detection of a single DNA base change are also important tools for genetic analysis. In many cases detection of a single base or a few bases would be a great help in genetic analysis since several genetic diseases and certain cancers are related to minor mutations.

Sequencing-by-synthesis methods are useful ways of determining the sequence of a DNA molecule of up to a hundred or more bases or the identity of a single nucleotide within a sample DNA molecule. During typical sequencing-by-synthesis methods the four different nucleotides (adenine, thymine, guanine and cytosine) are conveniently added cyclically in a specific order; when the base which forms a pair (according to the normal rules of base pairing, A-T and C-G) with the next base in the single-strand target sequence is added, it will be incorporated into the growing complementary strand by a polymerase and this incorporation will trigger a detectable signal. The event of incorporation can be detected directly or indirectly. In direct detection, nucleotides are usually fluorescently labelled allowing analysis by a fluorometer. (U.S. Pat. No. 48,638, 449, U.S. Pat. No. 5,302,509, Metzker et al. Nucl. Acids Res. (1994) 22: 4259–4267, Rosenthal International Patent Application No. WO 93/213401, WO 91/06678, Canard et al. Gene (1994) 148: 1–6). One such strategy of sequencing-by-synthesis called base addition sequencing scheme (BASS) is based on nucleotide analogues that terminate DNA synthesis. BASS involves repetitive cycles of incorporation of each successive nucleotide, in situ monitoring to identify the incorporated base, and deprotection to allow the next cycle of DNA synthesis.

Indirect detection usually takes advantage of enzymatic detection, e.g. measuring the release of PPi (inorganic pyrophosphate) during a polymerization reaction (WO 93/23564 and WO 89/09283). As each nucleotide is added to a growing nucleic acid strand during a polymerase reaction, a pyrophosphate molecule is released. It has been found that pyrophosphate released under these conditions can be detected enzymatically e.g. by the generation of light in the luciferase-luciferin reaction. Such methods enable a base to be identified in a target position and DNA to be sequenced simply and rapidly whilst avoiding the need for electrophoresis and the use of harmful radiolabels. These methods based on release of PPi are referred to herein as Pyrosequencing. The basic PPi-based sequencing methods have been improved by using a dATP analogue in place of dATP (WO 98/13523) and including a nucleotide-degrading enzyme such as apyrase during the polymerase reaction step, so that unincorporated nucleotides are degraded, as described in WO 98/28440.

However, these sequencing-by-synthesis methods mentioned above are not without drawbacks. A particular problem arises when the DNA to be sequenced has a number of identical adjacent bases, especially 3 or more the same. FIG. 1 shows the trace obtained when a single-stranded PCR product is sequenced according to known sequencing-by-synthesis methods (in this case involving detection of PPi). FIG. 1 shows that known methods do not provide clear results when two or more adjacent bases in the sample molecule are the same. For example, the peak height when the first set of three adenine residues are incorporated is almost the same as when four thymine residues are incorporated later; the set of three adenine residues incorporated around the middle of the sequence have the same peak height as previous doublets and the last pair of adenine residues to be incorporated have a peak height corresponding to single bases from the earlier part of the sequence.

Other problems of sequencing-by-synthesis methods include false signals which are the result of mispriming, i.e. hybridisation of the primer not to its targeted complement within the target DNA sequence but to another region which will result in generation of "incorporation signals" which do not reflect the identity of the target sequence. There is an associated problem which can result in a false indication of incorporation termed "minus frame incorporation", where a proportion of the growing primer originating strands are not fully extended and false positive signals appear in subsequent cycles.

Thus, there is a need further to improve sequencing-by-synthesis methods by addressing the above problems and more generally to improve the accuracy of the methods while providing methods which are simple and quick to perform, lending themselves readily to automation.

It has surprisingly been found that including a single-stranded nucleic acid binding protein in the reaction mixture improves the ratio of signals generated by one, two, three or more adjacent bases and reduces the number of false signals and generally improves the efficacy and reduces the cost of sequencing-by-synthesis methods.

In one aspect, the present invention thus provides a method of identifying a base at a target position in a sample nucleic acid sequence wherein a primer, which hybridises to the sample nucleic acid immediately adjacent to the target position, is provided and the sample nucleic acid and primer are subjected to a polymerase reaction in the presence of a nucleotide whereby the nucleotide will only become incorporated if it is complementary to the base in the target position, and said incorporation is detected, characterized in that, a single-stranded nucleic acid binding protein is included in the polymerase reaction step.

The nucleic acid to be sequenced may be any nucleotide sequence it is desirable to obtain sequence information about. Thus, it may be any polynucleotide, or indeed oligonucleotide sequence. The nucleic acid may be DNA or RNA, and may be natural, isolated or synthetic. Thus, the target DNA may be genomic DNA, or cDNA, or a PCR product or other amplicon etc. Alternatively, the target DNA may be synthetic, and genomic DNA, cDNA or a PCR product etc. may be used as primer. The target (sample) nucleic acid may be used in any convenient form, according to techniques known in the art e.g. isolated, cloned, amplified etc., and may be prepared for the sequencing reaction, as desired, according to techniques known in the art.

The DNA may also be single or double-stranded whilst a single-stranded DNA template has traditionally been used in sequencing reactions, or indeed in any primer-extension reaction, it is possible to use a double-stranded template; strand displacement, or a localised opening-up of the two DNA strands may take place to allow primer hybridisation and polymerase action to occur.

The sample nucleic acid acts as a template for possible polymerase based extension of the primer and thus may conveniently be referred to as "template" or "nucleic acid template".

In the polymerase reaction, any convenient polymerase enzyme may be used according to choice, as will be described in more detail below. In the case of a RNA template, such a polymerase enzyme may be a reverse transcriptase enzyme. The nucleotide may be any nucleotide sutiable for a polymerase chain extension reaction e.g. a deoxynucleotide or a dideoxynucleotide. The nucleotide may optionally be labelled in order to aid or facilitate detection of nucleotide incorporation. One or more nucleotides may be used.

Nucleotide incorporation by the action of the polymerase enzyme may be detected directly or indirectly, and methods for this are well known in the art. Representative methods are described for example in U.S. Pat. No. 4,863,879 of Melamede. As mentioned above, detection of incorporation may be by means of labelled nucleotides, for example fluorescently labelled nucleotides, as is well known in sequencing procedures known in the art. Alternatively, the event of incorporation may be detected by other means e.g. indirectly. Detection of incorporation also includes the detection of absence of incorporation e.g. lack of a signal. Thus, it may be detected whether or not nucleotide incorporation takes place.

The method of the invention thus has utility in a number of different sequencing methods and formats, including mini-sequencing procedures e.g. detection of single base changes (for example, in detecting point mutations, or polymorphisms, or allelic variations etc). The method of the invention may thus be used in a "full" sequencing procedure, ie. the identification of the sequential order of the bases in a stretch of nucleotides, as well in single base detection procedures.

For example, to determine sequence information in a target nucleotide sequence, different deoxynucleotides or dideoxynucleotides may be added either to separate aliquots of sample-primer mixture or successively to the same sample-primer mixture and subjected to the polymerase reaction to indicate which deoxynucleotide or dideoxynucleotide is incorporated.

In order to sequence the target DNA, the procedure may be repeated one or more times i.e. cyclically, as is known in the art. In this way the identity of many bases in the sample nucleic acid may be identified, essentially in the same reaction.

Hence, a sequencing protocol may involve annealing a primer as described above, performing a polymerase-catalysed primer extension step, detecting the presence or absence of incorporation, and repeating the nucleotide addition and primer extension steps etc. one or more times. As discussed above, nucleotides may be added singly or individually, or in a mixture, successively to the same primer-template mixture, or to separate aliquots of primer-template mixture, or to separate aliquots of primer-template mixture etc. according to choice, and the sequence information it is desired to obtain.

The term "single-stranded nucleic acid binding protein" as used herein is intended to refer to the class of proteins collectively referred to by the term SSB (Ann. Rev. Biochem. [1986] 55 103–136 Chase et al.). SSB has the general property of preferential binding to single-stranded (ss) over double-stranded (ds) nucleic acid molecules. The class includes E. coli single-stranded binding protein (Eco SSB), T4 gene 32 protein (T4 gp32), T7 SSB, coliophage N4 SSB, T4 gene 44/62 protein, adenovirus DNA binding protein (AdDBP or AdSSB), calf thymus unwinding protein (UP1) and the like (Coleman et al. CRC Critical Reviews in Biochemistry, (1980) 7(3), 247–289 and p5 SSB from fi-29 DNA (Lindberg et al. J. Biol. Chem. (1989) 264 12700–08) (Nakashima et al. FEBS Lett. (1974) A43 125). Any functionally equivalent or analogous proteins for example derivatives or modifications of the above-mentioned proteins, may also be used. Eco SSB or derivatives thereof are particularly preferred for use in the methods of the present invention.

Thus, modified single-stranded nucleic acid binding proteins derived by isolation of mutants or by manipulation of cloned single-stranded nucleic acid binding proteins which maintain the advantageous properties described herein, are also contemplated for use in the methods of the invention.

The term "dideoxynucleotide" as used herein includes all 2'-deoxynucleotides in which the 3'-hydroxyl group is absent or modified and thus, while able to be added to the primer in the presence of the polymerase, is unable to enter into a subsequent polymerisation reaction.

As described above, the method of the invention may be performed in a number of ways, and has utility in a variety of sequencing protocols. Viewed more generally, the present invention can thus be seen to provide the use of a single-stranded nucleic acid binding protein in a nucleic acid sequencing-by-synthesis method. In particular, the single-stranded nucleic acid binding protein is used to bind to the nucleic acid template.

What is meant by a DNA sequencing-by-synthesis method is defined above, namely that sequence information is derived by detecting incorporation of a nucleotide in a primer extension reaction. As explained above, such sequencing-by-synthesis protocols, include not only "full" sequencing methods, but also mini-sequencing methods etc., yielding more limited sequence information.

Any sequencing-by-synthesis method, as described above, is suitable for use in the methods of the present invention but methods which rely on monitoring the release of inorganic pyrophosphate (PPi) are particularly preferred. In this case, incorporation of the nucleotide will be measured indirectly by enzymatic detection of released PPi.

PPi can be determined by many different methods and a number of enzymatic methods have been described in the literature (Reeves et al., (1969), Anal. Biochem., 28, 282–287; Guillory et al., (1971), Anal. Biochem., 39, 170–180; Johnson et al., (1968), Anal. Biochem., 15, 273; Cook et al., (1978), Anal. Biochem. 91, 557–565; and Drake et al., (1979), Anal. Biochem. 94, 117–120).

It is preferred to use luciferase and luciferin in combination to identify the release of pyrophosphate since the amount of light generated is substantially proportional to the amount of pyrophosphate released which, in turn, is directly proportional to the amount of base incorporated. The amount of light can readily be estimated by a suitable light sensitive device such as a luminometer.

Luciferin-luciferase reactions to detect the release of PPi are well known in the art. In particular, a method for continuous monitoring of PPi release based on the enzymes ATP sulphurylase and luciferase has been developed by Nyren and Lundin (Anal. Biochem., 151, 504–509, 1985) and termed ELIDA (Enzymatic Luminometric Inorganic Pyrophosphate Detection Assay). The use of the ELIDA method to detect PPi is preferred according to the present invention. The method may however be modified, for example by the use of a more thermostable luciferase (Kaliyama et al., 1994, Biosci. Biotech. Biochem., 58, 1170–1171). This method is based on the following reactions:

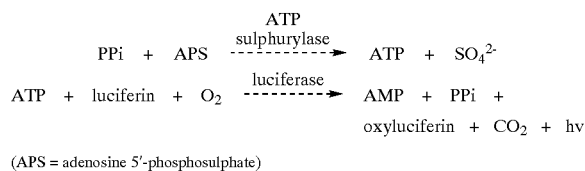

(APS = adenosine 5'-phosphosulphate)

The preferred detection enzymes involved in the PPi detection reaction are thus ATP sulphurylase and luciferase. Methods of detecting the light emitted are well known in the art.

In order to repeat the method cyclically and thereby sequence the sample nucleic acid and, also to aid separation of a single-stranded sample DNA from its complementary strand, it may be desirable that sample nucleic acid (DNA) is immobilised or provided with means for immobilisation attachment to a solid support.

Moreover, the amount of sample nucleic acid available may be small and it may therefore be desirable to amplify the sample nucleic acid before carrying out the method according to the invention.

The sample DNA may be amplified, for example in vitro by PCR, Self Sustained Sequence Replication (3SR), Rolling Circle Amplification or Replication (RCA or RCR), or indeed any other in vitro amplification technique, or in vivo using a vector and, if desired, in vitro and in vivo amplification may be used in combination. Whichever method of amplification is used, it may be convenient to adapt the method such that the amplified nucleic acid becomes immobilised or is provided with means for attachment to a solid support. For example, a PCR primer may be immobilised or be provided with means for attachment to a solid support. Also, a vector may comprise means for attachment to a solid support adjacent the site of insertion of the sample DNA such that the amplified sample DNA and the means for attachment may be excised together.

Immobilisation of the amplified DNA may take place as part of the amplification itself, e.g. in PCR where one or more primers are attached to a support, or alternatively one or more of the primers may carry means for immobilisation e.g. a functional group permitting subsequent immobilisation, e.g. a biotin or thiol group. Immobilisation by the 5' end of a primer allows the strand of DNA emanating from that primer to be attached to a solid support and have its 3' end remote from the support and available for subsequent hybridisation with the extension primer and chain extension by polymerase.

The solid support may conveniently take the form of microtitre wells, or dipsticks which may be made of polystyrene activated to bind the primer DNA (K Almer, Doctoral Theses, Royal Institute of Technology, Stockholm, Sweden, 1988). However, any solid support may conveniently be used, including any of the vast number described in the art, e.g. for separation/immobilisation reactions or solid phase assays. Thus, the support may also comprise particles, fibres or capillaries made, for example, of any polymer, e.g. agarose, cellulose, alginate, Teflon or polystyrene. Glass solid supports can also be used, e.g. glass plates or capillaries. Magnetic particles e.g. the superparamagnetic beads produced by Dynal AS (Oslo, Norway) are a preferred support since they can be readily isolated from a reaction mixture yet have superior reaction kinetics over many other forms of support.

The solid support may carry functional groups such as hydroxyl, carboxyl, aldehyde or amino groups, or other moieties such as avidin or streptavidin, for the attachment of primers or the target nucleic acid. These may in general be provided by treating the support to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. Sulphur and epoxy-based functional groups may also be used. U.S. Pat. No. 4,654,267 describes the introduction of many such surface coatings.

The assay technique is very simple and rapid, thus making it easy to automate by using a robot apparatus where a large number of samples may be rapidly analysed. Since the preferred detection and quantification is based on a luminometric reaction this can be easily followed spectrophotometrically. The use of luminometers is well known in the art and described in the literature.

As mentioned above, the sample nucleic acid, ie. the target nucleic acid to be sequenced, may be any nucleotide sequence, however obtained according to techniques known in the art, e.g. cloning, DNA isolation etc. It may for example be cDNA synthesised from RNA in the sample and the method of the invention is thus applicable to diagnosis on the basis of characteristic RNA. Such preliminary synthesis can be carried out by a preliminary treatment with a reverse transcriptase, conveniently in the same system of buffers and bases of subsequent amplification e.g. PCR steps, if used. Since the PCR procedure requires heating to effect strand separation, in the case of PCR the reverse transcriptase will be inactivated in the first PCR cycle. When mRNA is the sample nucleic acid, it may be advantageous to submit the initial sample, e.g. a serum sample, to treatment with an immobilised polydT oligonucleotide in order to retrieve all mRNA via the terminal polyA sequences thereof. Alternatively, a specific oligonucleotide sequence may be used to retrieve the RNA via a specific RNA sequence. The oligonucleotide can then serve as a primer for cDNA synthesis, as described in WO 89/0982.

Advantageously, the primer for the polymerase chain extension step (ie., the extension primer) is sufficiently large to provide appropriate hybridisation with the sequence immediately 5' of the target position, yet still reasonably short in order to avoid unnecessary chemical synthesis. It will be clear to persons skilled in the art that the size of the extension primer and the stability of hybridisation will be dependent to some degree on the ratio of A-T to C-G base pairings, since more hydrogen bonding is available in a C-G pairing. Also, the skilled person will consider the degree of homology between the extension primer to other parts of the amplified sequence and choose the degree of stringency accordingly. Guidance for such routine experimentation can be found in the literature, for example, Molecular Cloning: a laboratory manual by Sambrook, J., Fritsch E. F. and Maniatis, T. (1989).

The primer is conveniently added before the sample is divided into (four) aliquots although it may be added separately to each aliquot. It should be noted that the extension primer may be identical with the PCR primer but advantageously it may be different, to introduce a further element of specificity into the system.

Where appropriate, the polymerase reaction is carried out using a polymerase which will incorporate deoxynucleotides and dideoxynucleotides, e.g. T7 polymerase, Klenow, φ29 DNA polymerase or Sequenase Ver. 2.0 (USB U.S.A.). Any suitable polymerase may be used and many are known in the art and reported in the literature. However, it is known that many polymerases have a proof-reading or error checking ability and that 3' ends available for chain extension are sometimes digested by one or more nucleotides. If such digestion occurs in the method according to the invention the level of background noise increases. In order to avoid this potential problem, a nonproof-reading polymerase, e.g. T7 polymerase or Sequenase may be used. Otherwise it is desirable to add to each aliquot fluoride ions or nucleotide monophosphates which suppress 3' digestion by polymerase.

A fuller description of preferred embodiments of PPi based sequencing-by-synthesis methods are provided in WO 98/13523 and WO 98/28440 which are incorporated herein by reference. The use of a dATP analogue such as dATPαS in place of dATP is advantageous as it does not interfere with the detection reaction as it is capable of acting as a substrate for a polymerase but incapable of acting as a substrate for the PPi-detection enzyme luciferase. It is therefore possible to perform the chain extension and detection, or signal-generation, reactions substantially simultaneously by including the "detection enzymes" in the chain extension reaction mixture and therefore the sequencing reactions can be continuously monitored in real-time, with a signal being generated and detected, as each nucleotide is incorporated.

Inclusion of a nucleotide degrading enzyme in the reaction mix is also advantageous as it means that it is not necessary to wash the template thoroughly between each nucleotide addition to remove all non-incorporated deoxynucleotides, which has the associated benefit that a template can be sequenced which is not bound to a solid support.

In a particularly preferred method of the invention, the nucleotide-degrading enzyme apyrase is included during the polymerase reaction step and it has been found that the single-stranded binding proteins used in the methods of the present invention are able to stimulate the activity of apyrase. Whilst not wishing to be bound by theory, it is believed that the "SSB" may play a role in reducing the inhibition of apyrase which may be observed in the presence of DNA.

Thus in a further aspect, the present invention provides a method of enhancing the activity of a nucleotide-degrading enzyme when used in a nucleic acid sequencing-by-synthesis method, which comprises the use of a single-stranded nucleic acid binding protein. More particularly, the methods comprise including or adding a single-stranded nucleic acid binding protein to the sequencing reaction mixture (i.e. the template, primer, polymerase and/or nucleotide (e.g. dNTP/ddNTP) mix).

A similar enhancing effect has been observed on the luciferase enzyme which may be used in signal detection and therefore in a further aspect the present invention provides a method of enhancing the activity of luciferase when used as a detection enzyme in a nucleic acid sequencing-by-synthesis method which comprises the use of a single-stranded nucleic acid binding protein. Again, such methods involve including or adding a single-stranded nucleic acid binding protein to the sequencing reaction mixture.

In a preferred embodiment of the present invention the single-stranded nucleic acid binding protein is added after hybridisation of the primer to the template nucleic acid molecule.

It is also preferred, not to remove the single-stranded nucleic acid binding protein after it has been added.

It is a particular advantage of the present sequencing methods that there need be no separation of the different reagents and enzymes involved in the extension and detection reactions but the labelled or unlabelled nucleotides or nucleotide analogues, sample, polymerase and where appropriate enzymes and enzyme substrates, as well as the single-stranded nucleic acid binding protein can be included in the reaction mixture and there is no need to remove the single-stranded nucleic acid binding protein for detection to take place.

The reaction mixture for the polymerase chain extension step may optionally include additional ingredients or components if desired. Thus, such additional components can include other substances or molecules which bind to DNA. Thus, amines such as spermidine may be used. It was observed that improved results may be obtained using spermidine in run-off extension reactions.

Alternative additional components include DNA binding proteins such as RecA. In particular, it has been observed that a synergy occurs between RecA and a single-stranded nucleic acid binding protein, leading to improved results. Accordingly, the combination of RecA with a single-stranded nucleic acid binding protein represents a preferred embodiment according to the present invention. Other DNA binding proteins involved in DNA replication, recombination, or structural organisation may also be used in similar manner.

Other components which may be included, particularly when a double stranded substrate is used, include DMSO and formamide, and other agents which may destabilise or assist in destabilising double-strand formation, for example accessory proteins involved in DNA replication such as helicase.

When a single strand nucleic acid binding protein is used in accordance with the methods of the present invention, the methods are robust and results are readily reproducible. The read-length, i.e. the length of nucleic acid which can be successfully sequenced, has been increased by four times as compared to previous sequencing-by-synthesis methods. The methods of the invention are suitable for midi-sequencing, ie. the sequencing of nucleic acid molecules having 9–50 bases, mini-sequencing, the detection of single bases such as SNPs (single nucleotide polymorphisms) responsible for genetic diseases and the sequencing of nucleic acid molecules of 100 bases or more. It is in the successful sequencing of larger molecules that the benefits of a single strand nucleic acid binding protein in, particularly PPi based, sequencing methods are observed. The problems of maintaining a constant signal intensity for incorporation of one nucleotide, two nucleotides and so on, throughout the whole sequencing run are overcome.

In particular, the present invention may advantageously be used in the sequencing of 25 or more, advantageously 30 or more, 50 or more, or 60 or more bases.

As well as increasing the read length, the use of a single stranded nucleic acid binding protein enables the use of longer template molecules. Thus, sequence information from e.g. a 50 base region within a template molecule of 400 or more bases can be obtained. Template molecules of 800 or more, even 1200 or 1500 or more bases can be used in the methods of the present invention.

The amount of sequencing template accessible for the sequencing reaction may be reduced due to specific and/or unspecific interactions between the template and components of the reaction mixture and/or the surface of the vessel holding the reaction mixture. Such interaction may result in the reduction of the detected signal and/or generation of unspecific sequencing signal. SSB is believed to protect the template from such undesirable interactions and thus improve signal intensity and specificity. Furthermore, the protein may assist in "opening-up" and/or maintaining or stabilising the "open" structure of a double-stranded template.

When using the sequencing methods of the invention to detect mutations in a nucleic acid molecule, the sequencing reaction may advantageously be run bidirectionally to confirm the mutation.

Moreover, a further beneficial feature of the present invention is the stimulation of Klenow polymerase which is observable using the single-stranded nucleic acid binding protein according to the methods described herein.

Thus in a further aspect, the present invention provides a method of maintaining a constant signal intensity during a method of nucleic acid sequencing-by-synthesis comprising the use of a single-stranded nucleic acid binding protein. More particularly, the methods comprise including or adding a single-stranded nucleic acid binding protein to the sequencing reaction mixture (i.e. the template, primer, polymerase and/or nucleotide (e.g. dNTP/ddNTP) mix).

It is to be understood that 'constant signal intensity' in this context means that the strength of the signal, however measured, which indicates incorporation of the correct base-pair nucleotide remains substantially the same throughout the sequencing reaction, whether it is the first nucleotide incorporated, the twentieth or the sixtieth etc. Similarly, the strength of signal indicating incorporation of two nucleotides (ie. two adjacent bases are the same in the molecule to be sequenced) remains constant throughout the whole sequencing reaction and so on for three bases, four bases etc.

The single-stranded nucleic acid binding protein is present in the 'reaction mixture', i.e. together with the reagents, enzymes, buffers, primer, sample etc. which may include a solid support and is the site of polymerisation and also, where appropriate, detection.

A further benefit of the use of a single-stranded nucleic acid binding protein in accordance with the present invention is the relatively small amount of sample nucleic acid which is required for generation of useful sequence information. Approximately 0.05 pmol DNA in a 50 µl reaction is sufficient to obtain sequence information which means the quantity of enzymes needed for carrying out the extension reactions is less per cycle of nucleotide additions and per full sequencing reaction.

In a further aspect, the present invention provides a kit for use. in a method of sequencing-by-synthesis which comprises nucleotides for incorporation, a polymerase, means (e.g. any reagents and enzymes needed) for detection of incorporation and a single-stranded nucleic acid binding protein.

BRIEF DESCRIPTION OF THE DRAWINGS

The invention will now be described by way of non-limiting Examples with reference to the Figures in which.

EXAMPLE 1

Comparison of Sequencing Using *E. coli* SSB, SSB from T4 Phase (T4gp32) and no SSB Pyrosequencing was performed on approximately 0.2 pmol of a 405-base-long single-stranded PCR product obtained from mitochondrial DNA hybridised to 2 pmol of sequencing primer pH3A (5'-GCTGTACTTGC-TTGTAAGC). Primed DNA template together with 2 µg of SSB from *E. coli* (Amersham Pharmacia Biotech, Uppsala, Sweden) or 2 µg of T4gp32 (Amersham Pharmacia Biotech) was added to a four-enzyme-mixture comprising 6 U DNA polymerase (exonuclease-deficient Klenow DNA polymerase), 20 mU ATP sulfurylase, 200 µng firefly luciferase, and 50 mU apyrase.

Figure 1:
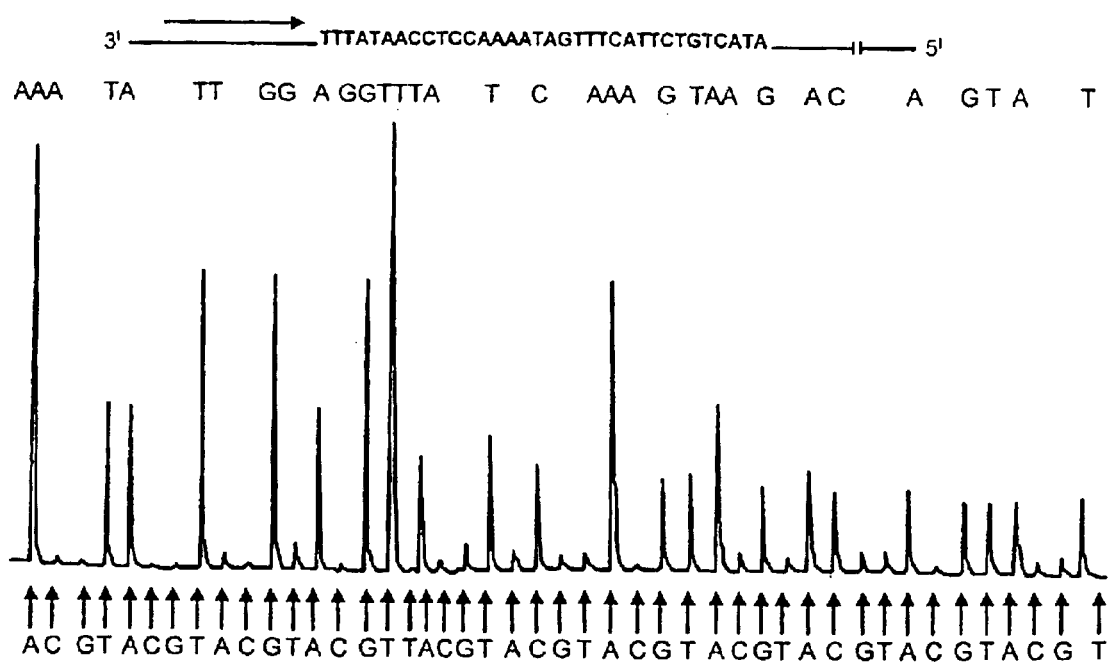
FIG. 1 shows a sequencing method of the prior art performed on a 130-base-long single-stranded PCR product hybridized to the sequencing primer. About 2 pmol of the template/primer was used in the assay. The reaction was started by the addition of 0.6 nmol of the indicated deoxynucleotide and the PPi released was detected. The DNA-sequence after the primer is indicated in the Figure.
Figure 2:
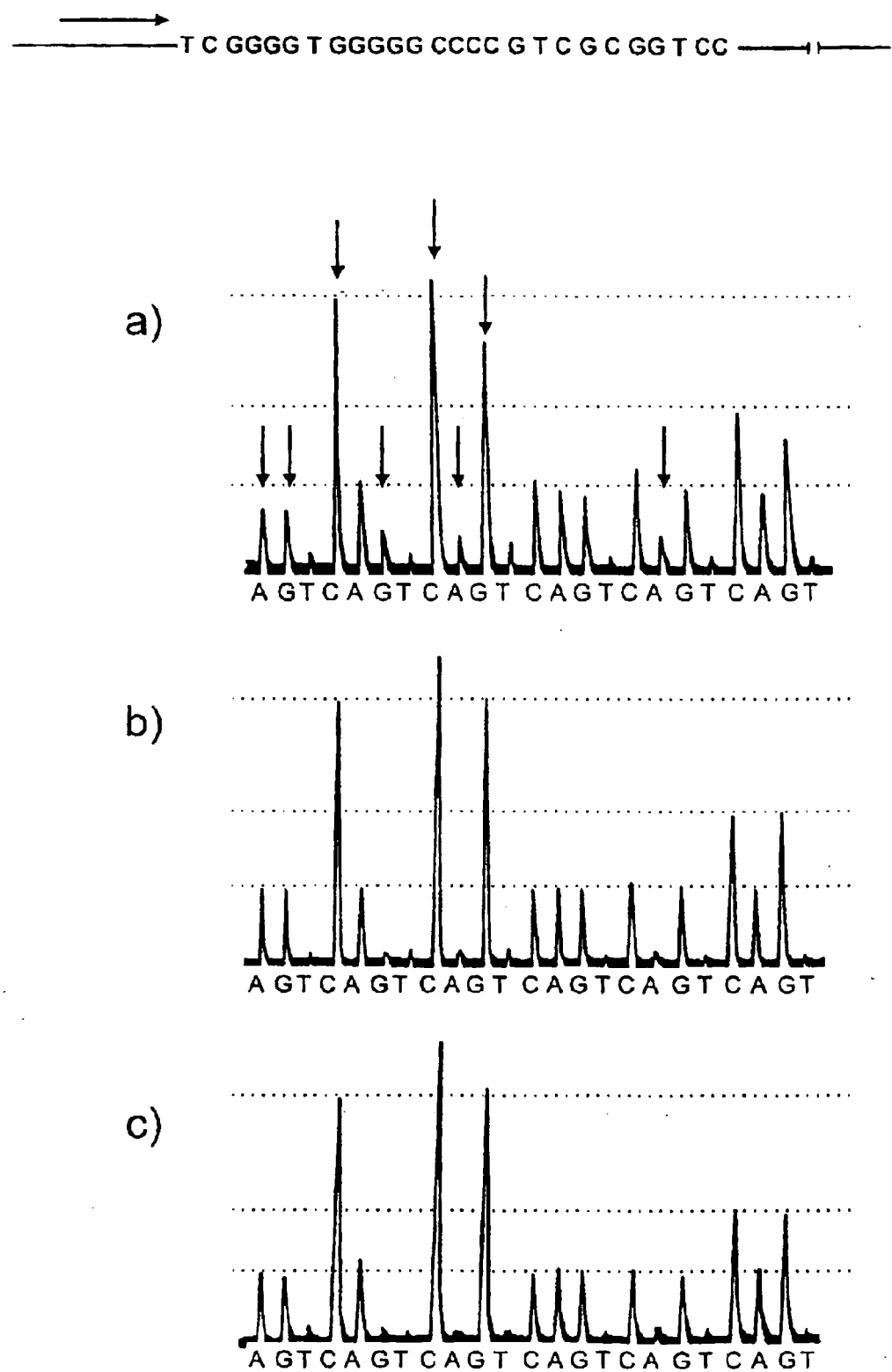
FIG. 2 shows Pyrosequencing of a PCR product a) in the absence of a single-stranded DNA binding protein, b) in the presence of SSB from T4 phage (T4gp32), and c) in the presence of SSB from *E. coli*. Lower quality of sequence data is obtained in the absence of SSB as indicated by arrows.

The sequencing procedure was carried out by stepwise elongation of the primer-strand upon sequential addition of the different deoxynucleoside triphosphates (Pharmacia Biotech). The reaction was carried out at room temperature. Light was detected by a Pyrosequencer (Pyrosequencing AB, Uppsala, Sweden) as described by Ronaghi et al. (Science 1998, 281: 363–365). See FIG. 2. Unincorporated nucleotides were degraded by apyrase allowing sequential addition of the four different nucleotides in an iterative manner. For this Example the correct sequence is:
5'-AGCCCCACCCCCGGGGCAGCGCCAGG.

EXAMPLE 2

Detection of Mutations

Figure 3:
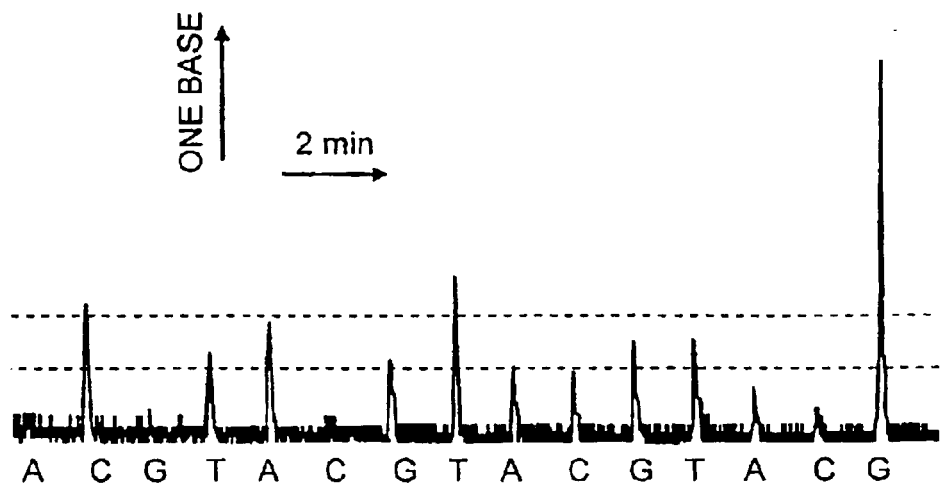
FIG. 3 shows a) the sequencing of mutated p53 template in the absence of a single strand DNA binding protein and b) sequencing of the same sequence when SSB is included.
Figure 3:
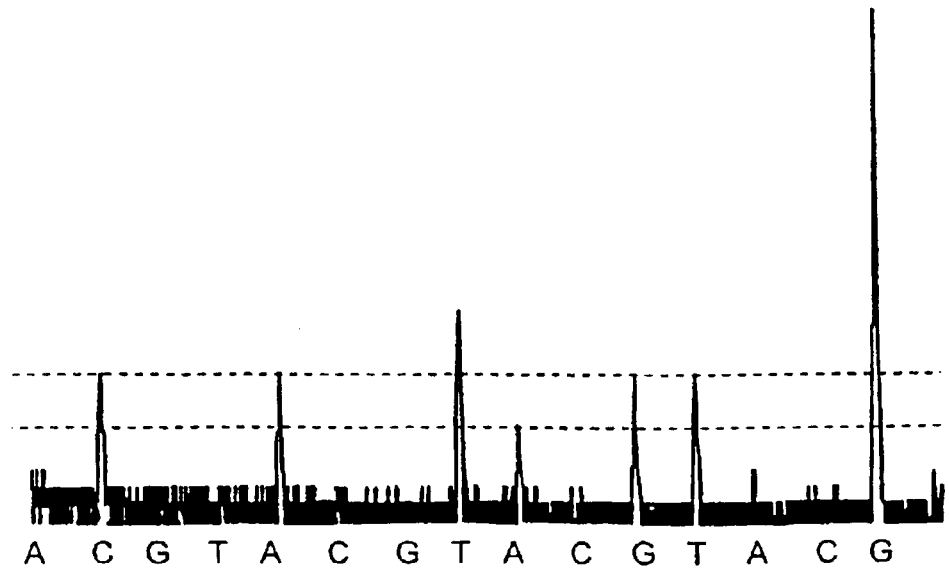

For mutation detection by Pyrosequencing, 2 pmol of primer COMP53 (5'-GCTATCTGAGCAGCGCTCA) was hybridised to the immobilised single-stranded PCR products obtained from exon 5 of p53 gene from normal and tumour tissues. 1/10 of the template obtained from a PCR product was used in a Pyrosequencing reaction and released light detected as described by Ronaghi et al.(Science 1998, 281: 363–365). There are two altered bases in the mutated template whch can be seen by a signal corresponding to 1.5 bases for T, 0.5 bases for A and 1 base for G. See FIG. 3. The sequence for this Example is 5'-CAT(TA/GG)TGGGGG.

EXAMPLE 3

Stimulation by SSB of Klenow Polymerase Activity

Figure 4:
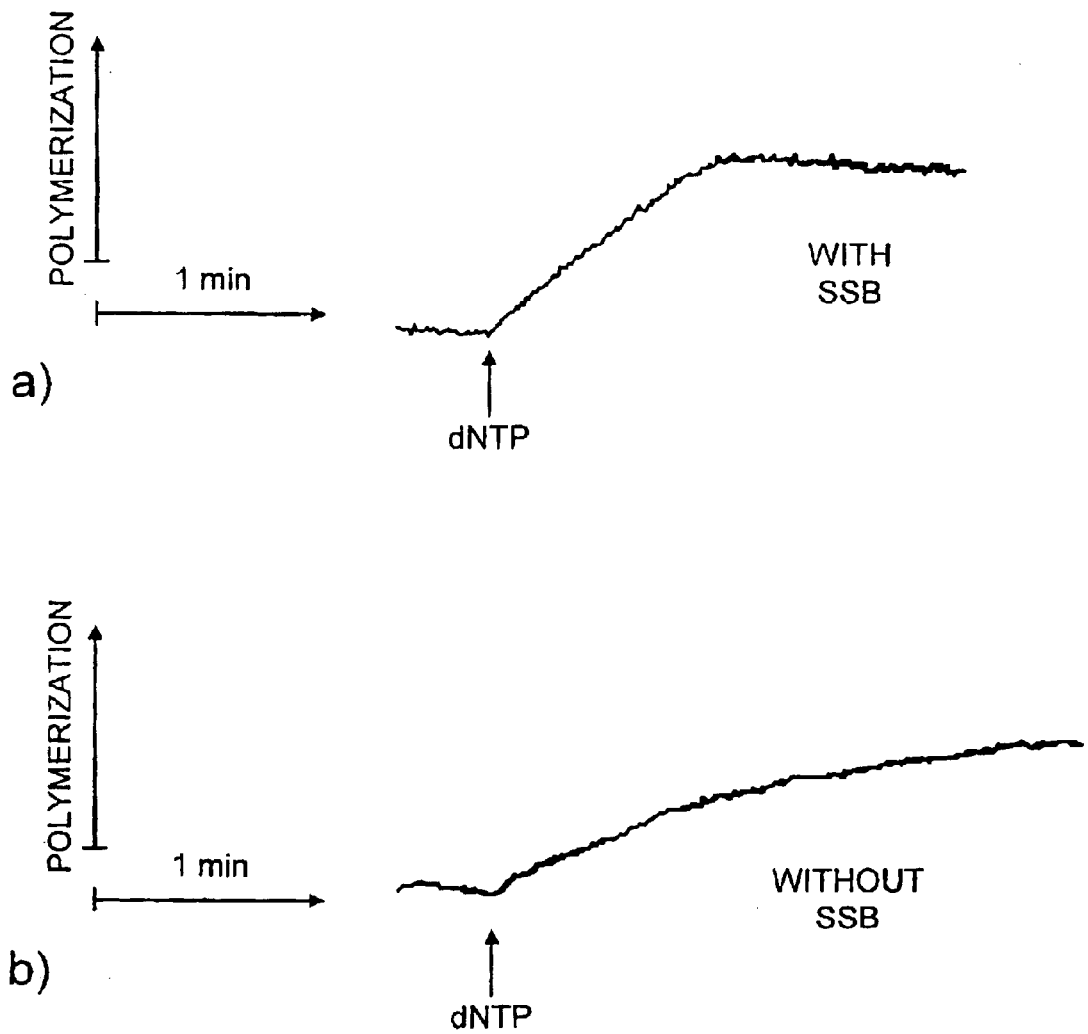
FIG. 4 shows a run off extension signal obtained on a 1500 bp long PCR fragment using Klenow DNA polymerase. A) in the presence of SSB and B) in the absence of a single-stranded DNA binding protein.

A run off extension signal was obtained on a 1500 bp long PCR fragment using Klenow DNA polymerase in the presence of SSB and in the absence of SSB. PCR was performed on 16S rNA gene with ENV1 (U1 universal primer *E. coli* positions 8–27) 5'-AGAGTTTGATIITGGCTCAG and ENV2B (U8 universal primer *E. coli* positions 1515–1493) 51-B-CGGITACCTTGTTACGACTT. After alkali treatment, the obtained single-stranded template (1/20 of a PCR product) was hybridised to 0.5 pmol of ENV1 primer for a run off extension reaction. 0.5 µg of *E. coli* SSB was added before extension using a coupled enzymatic reaction as described by Nyrén et al. (Anal. Biochem. 1997 244, 367–373). See FIG. 4.

EXAMPLE 4

Figure 5:
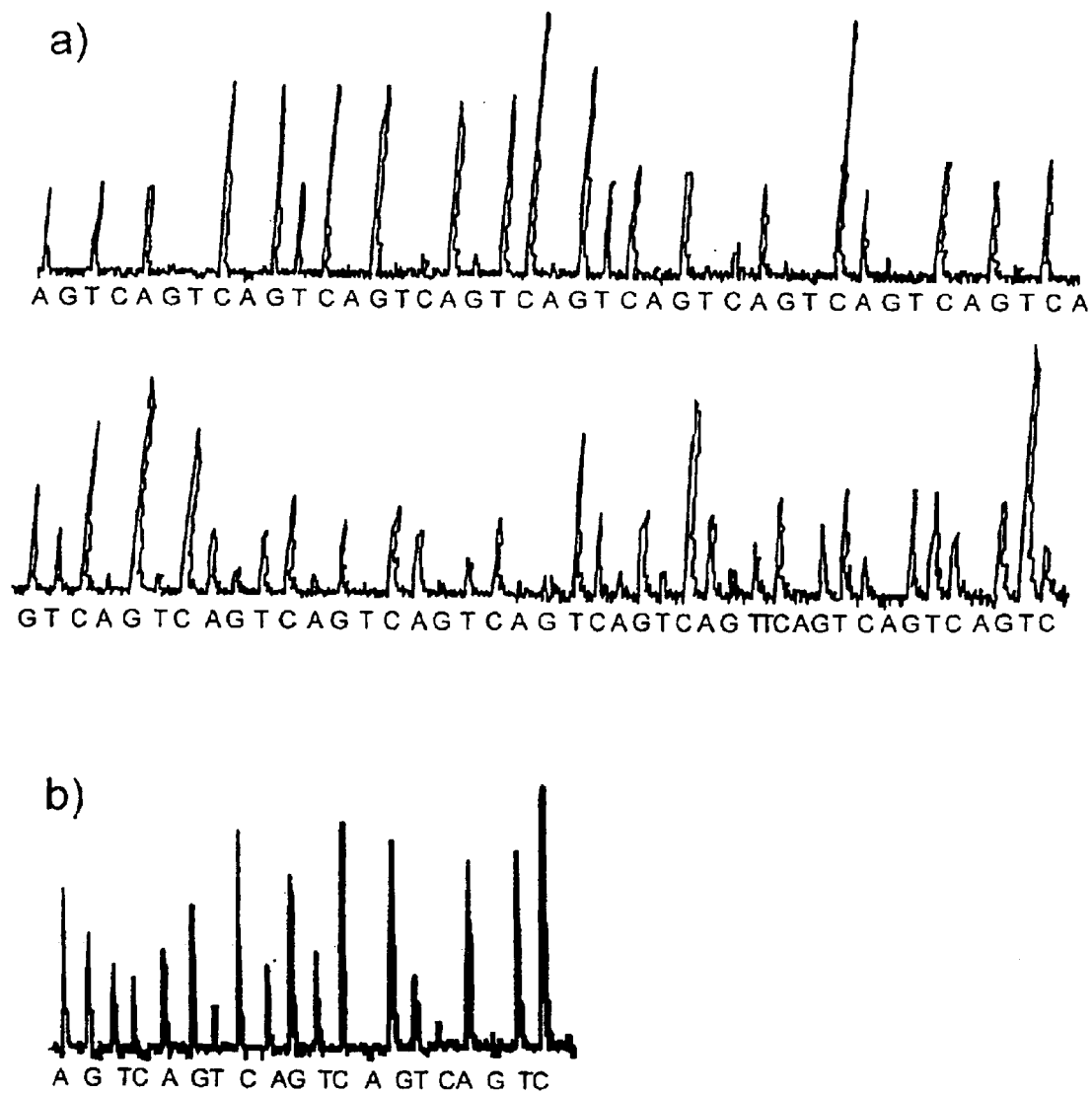
FIG. 5 shows the result of Pyrosequencing an 800 bp long PCR template a) in the presence of SSB and b) in the absence of a single-stranded DNA binding protein.

Pyrosequencing of an 800 bp Long PCR template in the Presence of SSB, and in the Absence of SSB Pyrosequencing was performed on an 800-base-long single-stranded PCR product hybridised to the sequencing primer FSS-SEQ-DOWN(5'-CTGCTCGGGCCC-AGATCTG). Two µg of SSB from *E. coli* was added to the template/primer (1/5 of a PCR product in which 5 pmol of primers have been used for in vitro amplification) and the obtained complex was used in a Pyrosequencing reaction as described by Ronaghi et al. (Science 1998, 281: 363–365). The sequence obtained by Pyrosequencing using SSB is as follows: ATACCGGTCCGGAATTCCCGGTCGACCC-ACGCGCCGGGCCATCGCACTTCGCCCACGT-GTCGTTTTC). See FIG. 5.

EXAMPLE 5

Inhibition of Apyrase by SSB in Presence of DNA

Figure 6:
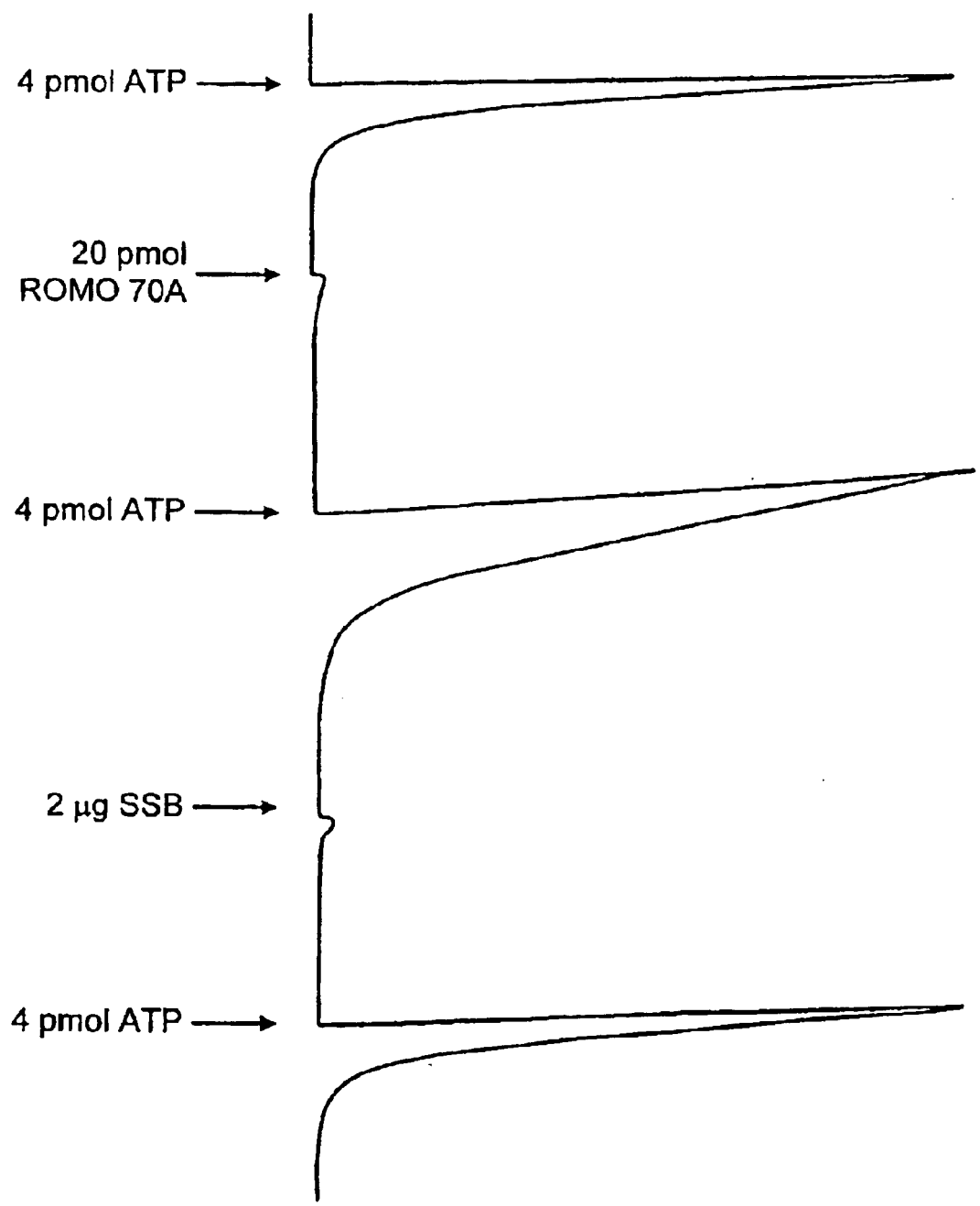
FIG. 6 shows, schematically, inhibition of apyrase in the presence of DNA and the ability of SSB to reduce the interaction of apyrase with the DNA.

To a Pyrosequencing mixture containing 200 ng luciferase and 50 mU apyrase, is added 4 pmol of ATP, and a signal is obtained. When the degradation curve reaches the base-line, 20 pmol of Romo70A (a 70-base-long oligonucleotide) is added to the solution (nucleotide degradation is inhibited 2.2 times by apyrase shown by a longer time needed to level off to the base line). When 2 µg of SSB is added to the solution, the interaction of the apyrase with the DNA is diminished and apyrase freely functions in the solution and a similar signal as before oligonucleotide addition is obtained. Further addition of 4 pmol ATP shows approximately the same degradation rate as before oligonucleotide addition to the solution. SSB is thus effectively able to stimulate apyrase activity. See FIG. 6.

EXAMPLE 6

Role of SSB in Maintaining a Constant Signal During the Sequencing Reaction

Figure 7:
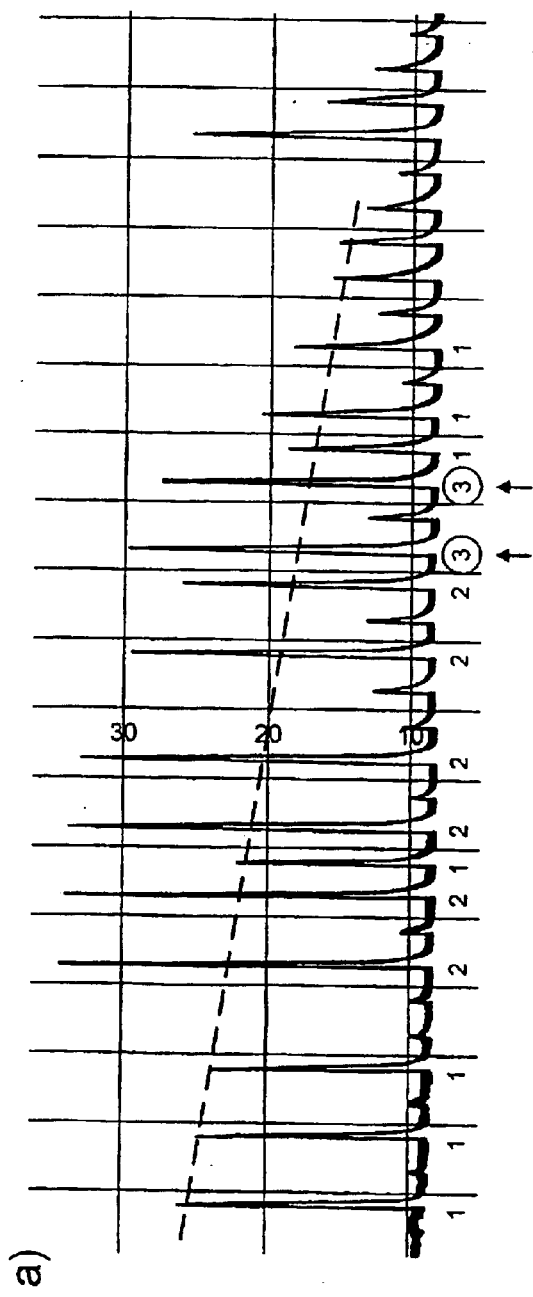
FIG. 7 shows the Pyrosequencing of a 450 bp cDNA template A) in the absence of a single strand DNA binding protein and B) in the presence of SSB. The numbers underneath the peaks show the number of bases incorporated. In A) the dashed line indicates how the strength of signal which results from the incorporation of one base decreases as the sequencing reaction progresses. In B) the dashed lines indicate how the strength of signal as one or two bases are incorporated remains constant when the reaction is carried out in the presence of SSB.
Figure 7:
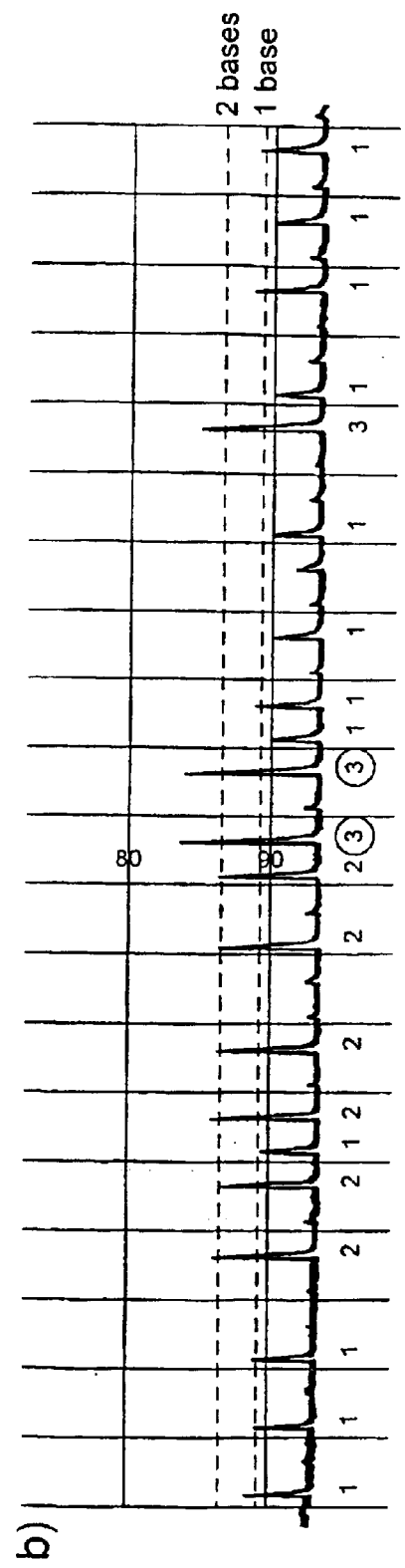

Pyrosequencing of a 450 base-long cDNA template obtained by PCR using universal primers was performed in the absence of SSB, and in the presence of SSB. The 450 bp single-stranded PCR product was hybridized to the sequencing primer FSS-SEQ-DOWN(5'-CTGCTCGGGCC-CAGATCTG). 2 µg of SSB from *E. coli* was added to the template/primer (1/5 of a PCR product in which 5 pmol of primers have been used for in vitro amplification) and the obtained complex was used in a Pyrosequencing reaction as described by Ronaghi et al. (Science 1998, 281:363–365). The sequence obtained by Pyrosequencing using SSB is: ATACCGGTCCGGAATTCCCGGGTCGACCCACGCA See FIG. 7.

What is claimed is:

1. A method of identifying a base at a target position in a sample nucleic acid sequence, comprising providing a sample nucleic acid and a primer which hybridizes to the sample nucleic acid immediately adjacent to the target position, subjecting the sample nucleic acid and primer to a polymerase reaction in the presence of a nucleotide whereby the nucleotide will only become incorporated if it is complementary to the base in the target position, and detecting said incorporation of the nucleotide by monitoring the release of inorganic pyrophosphate, whereby detection of incorporation of said nucleotide is indicative of identification of a base at a target position that is complementary to said nucleotide, and wherein a single-stranded nucleic acid binding protein is included in the polymerase reaction step, and is added after hybridization of the primer to the sample nucleic acid.

2. A method as claimed in claim 1 wherein the single-stranded nucleic acid binding protein is selected from the group consisting of *E. coli* single-stranded binding protein (Eco SSB), T4 gene 32 protein (T4 gp32), T7 SSB, coliphage N4 SSB, T4 gene 44/62 protein, adenovirus DNA binding protein (AdDBP or AdSSB) and calf thymus unwinding protein (UP1).

3. A method as claimed in claim 2 wherein the single-stranded nucleic acid binding protein is Eco SSB.

4. A method as claimed in claim 1 wherein the sample nucleic acid is DNA.

5. A method as claimed in claim 1 wherein the single-stranded nucleic acid binding protein binds to the sample nucleic acid.

6. A method as claimed in claim 1 wherein the release of inorganic pyrophosphate is detected using ATP sulphurylase and luciferase.

7. A method as claimed in claim 1 wherein apyrase is present during the polymerase reaction.

8. A method as claimed in claim 1 wherein at least 25 bases in the nucleic acid sample are identified.

9. A kit for use in a method of sequencing-by-synthesis which comprises nucleotides for incorporation, a polymerase, luciferase and a single-stranded nucleic acid binding protein.

\* \* \* \* \*